United States Patent
Even-Zohar

(10) Patent No.: US 8,452,458 B2
(45) Date of Patent: May 28, 2013

(54) METHOD AND SYSTEM FOR REAL TIME INTERACTIVE DYNAMIC ALIGNMENT OF PROSTHETICS

(75) Inventor: Oshri Even-Zohar, Amsterdam (NL)

(73) Assignee: Motek BV, Amsterdam (NL)

( * ) Notice: Subject to any disclaimer, the term of this patent is extended or adjusted under 35 U.S.C. 154(b) by 621 days.

(21) Appl. No.: 12/598,462

(22) PCT Filed: May 5, 2008

(86) PCT No.: PCT/IB2008/001835
§ 371 (c)(1), (2), (4) Date: Nov. 2, 2009

(87) PCT Pub. No.: WO2008/135863
PCT Pub. Date: Nov. 13, 2008

(65) Prior Publication Data
US 2010/0131113 A1 May 27, 2010

Related U.S. Application Data

(60) Provisional application No. 60/915,780, filed on May 3, 2007.

(51) Int. Cl.
G05B 13/00 (2006.01)
(52) U.S. Cl.
USPC ............... 700/279; 700/98; 700/117; 623/24; 607/2
(58) Field of Classification Search
USPC ................... 700/98, 117, 279; 623/24; 607/2
See application file for complete search history.

(56) References Cited

U.S. PATENT DOCUMENTS

| | | |
|---|---|---|
| 5,623,428 A | 4/1997 | Kunii |
| 5,623,944 A | 4/1997 | Nashner |
| 5,625,577 A | 4/1997 | Kunii |
| 5,791,351 A | 8/1998 | Curchod |
| 5,826,578 A | 10/1998 | Curchod |
| 5,872,858 A | 2/1999 | Kamada et al. |
| 5,904,484 A | 5/1999 | Burns |
| 5,930,741 A | 7/1999 | Kramer |
| 5,937,081 A | 8/1999 | O'Brill |
| 6,102,832 A | 8/2000 | Tani |
| 6,119,516 A | 9/2000 | Hock |
| 6,738,065 B1 | 5/2004 | Even-Zohar |
| 6,774,885 B1 | 8/2004 | Even-Zohar |
| 7,136,722 B2 | 11/2006 | Nakamura |
| 7,292,151 B2 | 11/2007 | Ferguson |
| 7,308,826 B2 | 12/2007 | Nakamura |
| 7,554,549 B2 | 6/2009 | Sagar |

(Continued)

OTHER PUBLICATIONS

PCT Search Report for PCT Application No. PCT/IB2008-001835, Jan. 16, 2009, 2 pages.

(Continued)

*Primary Examiner* — Mohammad Ali
*Assistant Examiner* — Anthony Whittington
(74) *Attorney, Agent, or Firm* — Maine Cernota & Rardin

(57) ABSTRACT

An objective method and system for dynamic analysis of prosthesis-bound subjects for determining optimal prosthesis alignment adjustments consists of a motion detection system, motion database, blending engine and algorithms, and a graphical user interface with suitable program controls whereby manual, semi-automatic, or fully automated analysis of a prosthesis-equipped subject's motion performance can be done in real time to determine objectively the optimal adjustments for the subject's prosthesis in a precise clinical protocol context.

20 Claims, 10 Drawing Sheets

U.S. PATENT DOCUMENTS

| | | | |
|---|---|---|---|
| 7,573,477 | B2 | 8/2009 | Ng-Thow-Hing |
| 2002/0045517 | A1 | 4/2002 | Oglesby |
| 2004/0071317 | A1* | 4/2004 | Pavlovie et al. ............. 382/103 |
| 2004/0256754 | A1 | 12/2004 | Koguchi |
| 2005/0240253 | A1* | 10/2005 | Tyler et al. .................... 607/134 |
| 2006/0135883 | A1* | 6/2006 | Jonsson et al. ................ 600/546 |
| 2006/0161218 | A1* | 7/2006 | Danilov .......................... 607/45 |
| 2006/0173259 | A1* | 8/2006 | Flaherty et al. .............. 600/331 |
| 2006/0206215 | A1* | 9/2006 | Clausen et al. ................. 623/24 |
| 2006/0241718 | A1* | 10/2006 | Tyler et al. ...................... 607/45 |
| 2006/0247904 | A1 | 11/2006 | Dariush |
| 2007/0103471 | A1* | 5/2007 | Yang et al. .................... 345/473 |
| 2007/0146371 | A1* | 6/2007 | Dariush ........................ 345/474 |
| 2007/0172797 | A1 | 7/2007 | Hada |
| 2007/0250119 | A1* | 10/2007 | Tyler et al. ........................ 607/2 |
| 2007/0255454 | A1* | 11/2007 | Dariush ........................ 700/245 |
| 2008/0009771 | A1* | 1/2008 | Perry et al. .................... 600/587 |
| 2008/0180448 | A1 | 7/2008 | Anguelov |
| 2008/0227545 | A1* | 9/2008 | Cho et al. ........................ 463/36 |
| 2009/0135189 | A1 | 5/2009 | Kim |

OTHER PUBLICATIONS

McLean, Scott G. et al., "Sagittal Plane Biomechanics Cannot Injure the ACL During Sidestep Cutting", Clinical Biomechanics, 2004, pp. 828-838, Elsevier Ltd.

De Leva, Paolo, "Adjustments to Zatsiorsky-Seluyanov's Segment Inertia Parameters", J. Biomechanics, 1996, pp. 1223-1230, vol. 29, No. 9, Elsevier Science Ltd., Great Britain.

Delp, Scott L. et al., "An Interactive Graphics-Based Model of the Lower Extremity to Study Orthopedic Surgical Procedures", IEEE Transactions on Biomedical Engineering, Aug. 1990, pp. 757-767, vol. 37, No. 8.

Van Den Bogert, Antonie J. et al., "A Weighted Least Squares Method for Inverse Dynamic Analysis", Computer Methods in Biomechanics and Biomedical Engineering, 2007, pp. 1-7, vol. 00, No. 0.

Xia, Youshen et al., "An Improved Neural Network for Convex Quadratic Optimization with Application to Real-Time Beamforming", Neurocomputing, 2005, pp. 359-374, Elsevier B.V.

Van Der Helm, F.C.T., "A Finite Element Musculoskeletal Model of the Shoulder Mechanism", J. Biomechanics, 1994, pp. 551-569, vol. 27, No. 5, Elsevier Science Ltd, Great Britain.

"Nonlinear Models", Cambridge University Press, 1986-1992, pp. 675-684.

Rule 132 Declaration for Itzhak Siev-Ner, MD for U.S. Appl. No. 11/832,726, 4 pages.

World Academy of Science, Engineering and Technology 45 2008 article entitled "Feature's Extraction of Human Body Composition in Images by Segmentation Method."

Symposium on Applied Computing archive, Proceedings of the 2002 ACM symposium on Applied computing, Madrid, Spain, Session: Virtual reality, digital media, and computer games table of contents, pp. 1074-1079, year of Publication: 2002 ISBN:1-58113-445-2.

Kovar, Lucas et al., Flexible Automatic Motion Blending with Registration Curves, Eurographics/SIGGRAPH Symposium on Computer Animation (2003), 11 pages.

Park, Sang Il et al., On-line Locomotion Generation Based on Motion Blending, in Proceedings of the 2002 ACM SIGGRAPH/Eurographics Symposium on Computer Animation, Jul. 2002, 8 pages.

Feng, Andrew et al., An Analysis of Motion Blending Techniques, he fifth international conference on Motion in Games, Rennes, France, Nov. 2012, 12 pages.

Ahmed, Amr et al., Parametric Motion Blending through Wavelet Analysis, EUROGRAPHICS 2001, 7 pages.

* cited by examiner

METHOD AND SYSTEM FOR REAL TIME INTERACTIVE DYNAMIC ALIGNMENT OF PROSTHETICS

RELATED APPLICATIONS

This application claims the benefit of U.S. Provisional Application No. 60/915,780, filed 3 May 2007, and is herein incorporated in its entirety by reference.

FIELD OF THE INVENTION

This invention most generally relates to a method and system for facilitating prosthetic adjustments. Motion sensors combined with motion blending algorithms and a three dimensional (3D) computational software engine create a real time environment where dynamic alignment of prosthetic limbs can be done in an objective and exact clinical protocol context.

BACKGROUND OF THE INVENTION

There are many tragic injuries and illnesses in the world, and one of the most vivid reminders of these is amputees. It is estimated that there are 70,000 major amputations performed annually in the United States alone, and more than 200 million amputations each year in the world. Many of these are major limb amputations of the lower extremities.

In an effort to improve the life of the amputee there has been significant research in developing artificial limbs that look and move more like actual human limbs. Advances in robotics, biomechanics, composites and computers have made great strides in realistic artificial limbs. Prosthesis is defined as an artificial extension that replaces a missing body part. An artificial limb is a type of prosthesis that replaces the missing body part, such as an arm and leg.

There are four main types of artificial limbs, namely transtibial, transfemoral, transradial, and transhumeral, wherein the prosthesis depends on what part of the limb is missing. The new plastics and composites which include carbon fiber provide for greater strength as well as greater design options using computer aided design.

Artificial limbs are typically manufactured by a process that that involves; Measurement of the stump area Body measurements to determine the artificial limb size; Creation of a model of the stump; Formation of a thermoplastic sheet around the model for fitting; Formation of a permanent socket; Formation of the plastic or composite parts of the artificial limb; Creation of metal parts of the artificial limb; and, Assembly of entire limb.

For illustrative purposes, a prosthetic leg includes a number of different elements that allow for the proper motion and to distribute the various forces. The first element is typically a liner that resides on the residual limb and attaches through a prosthetic lock to the other parts of the prosthesis. The liner is a soft stretchy material that protects the limb and acts as an interface between the socket and the limb.

The residual limb and liner are then coupled to a hard socket. The socket is specially made to fit the specific user and comes in a variety of materials. The socket is custom made to create a better fit between the residual leg and the artificial limb. The socket can be created by taking a plaster cast of the stump and then making a mold from the plaster cast, however other methods such as laser guided measuring can be utilized.

The additional elements for the leg prosthetic depend upon the prosthetic. For example, a transfemoral prosthesis has a prosthetic knee joint connected to the socket to allow for the knee flexure. A prosthetic foot is the last element and is designed with properties that allow for stability and movement to enable walking. In between the main elements of the prosthetic legs are smaller adapters that connect the main parts together and help in the proper alignment of the prosthesis. Many artificial limbs are attached to the stump of the amputee by belts and cuffs or by suction.

Current prosthetic alignment techniques are primarily based on visual estimation, and while there are some devices for static alignment, their tuning is modified after the dynamic alignment is done since leg loads are changed when moving the prosthetic. The muscle forces exerted by the human body on the prosthetic cannot be accurately taken in consideration when doing static alignment only, and dynamic alignment is typically the most important part of the process of prosthetics fitting.

The alignment practices for prosthetic devices vary, depending on the design characteristics of the prosthetic, the location of the artificial limb and the individual. However, the goal of alignment is to establish a stable and safe prosthetic limb. By way of illustration, the prosthetic knee components vary in design, shape, size, resistance to buckling, and swing characteristics.

Typically, the knee is aligned to center posterior to what is considered the reference or "weight bearing" line. The posterior placement creates an extensor moment at the knee, generally resulting in more stability. The alignment stability can be evaluated in the sagittal plane with respect to three commonly used reference lines, namely the European line, the trochanter, knee, and ankle (TKA) line, and the medial, knee, and ankle (MKA) line. The European line projects vertically along the lateral aspect of the limb, passing through the center of the socket brim and bisecting the horizontal length of the foot. The TKA line extends through the head of the greater trochanter, center of the knee, and the center of the ankle. The MKA line is the line from the medial center of the socket to the center of the knee to the center of the ankle.

The older static alignment processing used a vertical reference line formed by dropping a plum bob from the trochanter and measuring the position of the knee center and the ankle from that line. Newer alignment tools form a similar reference line by projecting a vertical laser line up from a force plate onto the patient. This projected laser line may indicate either the center of pressure or be translated to a landmark on the patient, such as the trochanter, thus applying a visual demarcation similar to a plumb line. Regardless of the initial static alignment, there is an ongoing dynamic alignment that addresses the actual load related changes required for an optimal fit.

As noted herein, most rehabilitation clinics and medical research institutes use specialized alignment protocols, based on 'cause' related classifications of movement disorders. There is currently no known objective way to get optimal alignment, as it is substantially based on subjective experience of the prosthetist. The results vary greatly between different clinics and rehabilitation hospitals, and often a patient that had his prosthetic limb aligned by one prosthetist will typically have to undergo a second and third repetition of the alignment process for optimal performance. At the present time, the state of the art does not seem to have a known system or method available for dynamically aligning accurately and objectively prosthetics such as prosthetic legs.

Modern prosthetic technologies are more complex but offer a greater span of dynamic function to the user when aligned properly. The C-Leg microprocessor prosthetics try to optimize function and take advantage of the unique characteristics afforded by microprocessor and software control.

For illustrative purposes, examples herein are provided with respect to walking. The term gait refers to the manner of walking, wherein a full gait cycle is defined as the time interval between two successive occurrences of one of the repetitive events of walking. There are typically seven identified major components to a full gait cycle, namely initial contact, opposite toe-off, midstance, heel rise, opposite initial contact, toe-off, feet adjacent, and tibia vertical.

The starting point in the gait cycle is typically at initial contact. For example, if the left foot is the starting point or reference, the cycle continues until the left foot makes initial contact again. The distance covered during this cycle is called a stride length, wherein a step length is one half the stride length.

The gait cycle components can be sub-divided into two phases, namely the stance phase and the swing phase. The stance phase occurs when the foot is making contact with the ground and involves the first four components of the gait cycle, namely initial contact, opposite toe-off, midstance and heel rise. The swing phase is when the foot is moving forward through the air and consists of the remaining components of the gait cycle, namely opposite initial contact, toe-off, feet adjacent, and tibia vertical.

Initial contact refers to heel contact, wherein the major role of the lower extremity is to absorb the impact forces created when the foot strikes the ground. The heel pad along with control of the ankle as the foot moves from the heel to the forefoot allows the absorption of the forces. On contact, the hip extensors, gluteus maximus, and hamstrings create internal extensor movement at the hip, and these muscles concentrically contract and propagate an extension force at the hip joint. Simultaneously, the knee undergoes an internal flexor moment secondary to the contraction of the hamstrings to block hyperextension at the end of the swing phase. The ankle is usually kept in the neutral position on initial contact in preparation for the next phase.

The loading response refers to the double support period between the initial contact and opposite toe-off components. The foot is lowered to the ground by means of plantarflexion of the ankle, which is simultaneously resisted by dorsiflexion produced by tibialis anterior. These actions maintain control of the foot and allow for a gentle lowering to the ground. At this point, the center of gravity is at its lowest point in the gait cycle.

After the loading response, opposite toe-off is the next component of the gait cycle and is the beginning of midstance and the first period of single support. The forefoot impacts the ground at about the same time opposite toe-off occurs. The hips move steadily through extension with power, while the knee generates an external flexor movement. The quadriceps muscles eccentrically contract, absorbing energy and allowing the knee to act like a spring. The direction of the ankles shifts from plantarflexion to dorsiflexion when the tibia passes over the stationary foot.

The term Midstance is defined as the period between opposite toe-off and heel rise. It signifies the moment when the swing-phase leg passes the stance-phase leg. During the period, the hip begins to lose its extensor movement with a decline in contraction of the gluteus maximus and hamstrings. The knee shifts its motion from flexion to extension and at the same time generates power. As the tibia moves forward over the ankle due to the inertia created by the trunk, it undergoes external rotation concomitant with forefoot supination. The ankle continues to shift from plantarflexion to dorsiflexion with the triceps surae muscle contracting eccentrically. The speed at which the center of mass of the body moves over the supporting stance-phase limb is regulated by the power created during plantarflexion of the ankle.

Heel rise is the next component of the gait cycle and represents the period when the heel begins to lift from the walking surface. A progressive internal flexor moment is created at the hip, while an internal flexor knee moment is initiated when the quadriceps muscles stops contracting before heel rise. The knee action occurs because the upper body moves faster that the tibia and because the triceps surae retards the forward motion of the tibia while the femur steadily moves forward. These motions create an external extensor moment opposed by an internal flexor moment at the knee. The ankle has an internal dorsiflexor moment as the soleus and the gastrocnemius begin to progressively contract.

The Opposite initial contact starts pre-swing with the start of opposite initial contact, the hip and knee begin to flex while the ankle is plantarflexing. The body now pivots on the forefoot instead of the ankle, which creates more power, and the triceps surae and other secondary ankle plantarflexors create a corresponding internal plantarflexor moment in response to the external dorsiflexor moment. These muscles use an eccentric contraction. The triceps surae is used to impede the body's momentum instead of launching it forward and allows favorable ankle stabilization and a decline in the amount of fall by the body's center of gravity. In addition, the adductor longus muscle acts as the primary hip flexor in this phase, and the rectus femoris muscle contracts eccentrically to stabilize knee flexion. All of these actions assist with forward acceleration of the leg into the swing phase.

The next component, toe-off, represents the end of the stance phase and the beginning of the swing phase. Muscle contraction changes from eccentric in stance phase to concentric in swing phase. Toe-off occurs at around 60% point of the gait cycle. An internal flexor moment occurs at the hip secondary to inertial forces and contraction of the adductor longus and iliopsoas muscles. The rectus femoris muscle contracts to prevent excessive knee flexion and the internal plantarflexion moment loses power at the ankle as the toe leaves the ground.

Following the toe-off component, the feet adjacent component is the next stage of the swing phase. Considerable power is generated at the hip by the rectus femoris, adductor, and iliopsoas muscles to move the leg forward through the swing phase. Eccentric contraction of the quadriceps continues throughout the first half of the swing phase to regulate the rate and extent of knee flexion. Some of the kinetic energy created through contraction and inertia is transferred to the trunk as the swing leg is decelerated at the end of this phase.

The final component of the gait cycle is tibia vertical, which is represented by the tibia of the swinging leg becoming vertical. This is the period between midswing and terminal swing. In this phase, the knee extends in preparation for the beginning of the stance phase. This extension is accomplished through two mechanisms, namely concentric contraction of the hip extensors which causes a posterior rotation at the thigh, and inertia created at the foot and shank which allows it to continue forward. Eccentric contractions of the hamstrings gradually decelerate the foot and shank until the knee arrives at an extended position. At this point, the swing phase leg not only is prepared for the next stance phase but also helped with trunk acceleration. As previously noted, some of the kinetic energy created during the swing phase is transferred to the trunk upon deceleration.

People who have undergone amputations generally incorporate different muscles and adaptive strategies to ensure a smooth and well-coordinated gait pattern. One of the underlying attributes in gait analyzing an amputee's gait is to try to use the least amount of energy to cover the greatest distance. Several factors are typically considered when thinking about the energy costs of prosthetic ambulation. One is the actual metabolic costs which is the peak exercise oxygen consumption [$VO_2$] in mL/kg/m) of the person who has undergone amputation compared to that of intact people. Increased metabolic cost for persons who have undergone amputations means the gait is inefficient compared to that of healthy intact persons, who require less endurance for any given distance.

A pathologic gait is inefficient and usually requires considerably more energy than a normal gait. Patients may adopt many kinds of abnormal movements to minimize their energy usage, which can be categorized into those involving energy transfers and those involving movements that minimize the displacement of the center of gravity. The optimizations or determinants of gait can be generally considered to be Pelvic rotation, Pelvic obliquity, Knee flexion in the stance phase, Ankle mechanisms, Foot mechanisms, and Lateral displacement of the body. In a general sense, these elements can be combined to create a smoother gait and reduced energy expenditure by minimizing the downward and lateral motion of the center of gravity.

Patients with various amputations have adopted strategies for minimizing their energy consumption in ambulation. In persons who have undergone TT (transtibial) amputations, the timing and magnitude of the muscular work patterns in the intact limb are correlated with a normal gait. However, the prosthetic limb must make up for the energy absorption of the quadriceps and triceps surae muscles and for the eccentric power generation of the triceps surae.

During the stance phase, the prosthetic limb performs about half of the work of normal muscle. Energy absorption by the knee extensors and energy generation by the prosthetic foot are substantially reduced. To offset the loss of power from triceps surae with roll-off, the person who has undergone amputation changes the biomechanics of both the prosthetic limb in the stance phase and the intact limb during the swing phase. In the prosthetic limb, the primary energy absorbers and generators shift to the hip extensors during the stance phase. Also, during swing phase, the muscular work components substantially increase in the intact limb. The excess mechanical work is ultimately transmitted to the trunk during terminal swing-phase deceleration. The increase in the forward momentum of the trunk compensates for the loss of power generation with the prosthetic foot.

The person who has undergone TF (transfemoral) amputation must deal with the loss of the foot, ankle, and the knee. The biggest apprehension of the person who has undergone TF amputation is the prevention of knee buckling. Besides the actual prosthetic hardware and knee alignment to add stability, the biomechanics of the gait are changed to provide additional stability. The person who has undergone TF amputation does not allow knee flexion in the first 30-40% of the stance phase. This limitation minimizes the likelihood of knee buckling. In addition, the hip extensors help maintain hip extension through closed kinetic chain mechanisms.

In the opposite initial contact part of the gait cycle, the ankle plantarflexors, particularly the triceps surae and the hip flexors, contract to generate power for the acceleration of the leg forward into the swing phase. Although the prosthetic limb is only a fraction of its normal mass with a TF amputation, the hip flexors must generate the same power as a normal limb. The intact limb adjusts to compensate for the prosthetic limb in these cases.

During the stance phase in the intact limb, generated energy is augmented by the hip extensors and the ankle plantarflexors. In this way, person who has undergone amputation tries to offset the loss of power from the triceps surae in the prosthetic limb. During the swing phase, the biomechanics of the person who has undergone TF amputation mimics those of normal gait, including the energy-absorbing function of the quadriceps performed through the prosthetic hydraulic knee unit.

The common gait deviations of TT and TF prosthetic gait are briefly addressed in terms of the types of amputation and the times at which the deviations occur in the gait cycle.

Stance-phase problems can occur in the gait of individuals with a TT prosthetic. Inappropriate knee flexion can occur in the early stance phase, causing knee instability. Several problems could arise from this flexion, including excessive ankle dorsiflexion, socket flexion, and posterior foot placement. Knee hyperextension could also occur in the early stance phase, emanating from ankle plantarflexion or socket extension, weak knee extensors, anterior foot placement, or inadequate prosthetic foot selection.

Mediolateral knee thrust can also be observed in the stance phase. This is usually derived from inadequate side-to-side placement of the foot, excessive angulation of the socket, or wide mediolateral proximal socket dimensions that cause decreased knee control. If an individual who has undergone a TT amputation is noted to have a foot slap in his or her gait, it may be a result of excessive socket flexion or foot dorsiflexion, the uneven placement of the foot, or a deficient heel height for proper prosthetic alignment. Excessive forward progression of the tibia, or a drop-off gait can be caused by impaired rollover, shortening of the contralateral step length and swing time, and delayed heel-off.

External rotation can occur at two different phases of the gait cycle: heel strike or late stance. If external rotation occurs during heel strike, the etiology could be a solid ankle cushion heel (SACH) durometer that is too dense, an articulated foot plantarflexion bumper that is too hard, or misplacement of the suspension cuff-retention points. If external rotation occurs in late stance, it can be caused by inadequate excessive anterior placement of the foot, excessive foot plantarflexion, or excessive hardness of the forefoot.

Early heel rise could result from inadequate placement of the foot (posterior), flexion contracture in the hip or the knee that was not accounted for in fitting the prosthetic, or excessive softness of the forefoot. Contralateral early heel rise or vaulting is a pathologic gait that allows clearance of the prosthetic limb with decreased hip and knee flexion. Vaulting compensates for a prosthesis that is too long, inadequate suspension of the prosthesis, or a learned gait pattern.

Fewer gait problems are involved with the swing phase than with the stance phase. The objective of the swing phase is forward advancement of the non-weightbearing limb. When prosthetic limb clearance is poor, the gait becomes pathologic. Most predicaments occur because of poor suspension, a prosthesis that is too long, insufficient prosthetic knee flexion, or inadequate transfer of power from the residual limb to the prosthesis that decreases or delays knee flexion. A coordinated, smooth, swing phase is facilitated by energy-efficient limb clearance, which is enabled by synchronized motion at the hip and knee joints and by total joint displacement.

Foot drag is one of the most common problems of swing phase. It is usually caused by inadequate suspension of the prosthesis, a prosthesis that is too long, or lower-limb weakness in the hip abductors or ankle plantarflexors on the contralateral side. Any abnormal limb rotation is observed during the gait trial is usually caused by insufficient suspension of the prosthesis, misplacement of the suspension cuff-retention points, or overshooting of the hip or knee flexors to evade foot drop.

Limited knee extension or flexion problems can always be traced back to mechanical contractures, problems with the suspension, or problems with the knee joint in relation to a thigh corset.

The gait deviations in persons who have undergone TF amputations differ from those of people who have undergone TT amputations in a couple ways. As alluded to previously, knee flexion in the stance phase is one of the most common problems related to gait instability with TF amputations. If a patient with a TF amputation is concerned about putting weight on the prosthetic leg because the knee flexion moment creates instability, an inefficient gait pattern results. For these patients, one of several unique models of prosthetic knees can be prescribed based on his or her individual needs.

Additional etiologies of knee flexion in stance are a hard SACH durometer, excessive foot dorsiflexion, excessive socket flexion, weak hip extensors, or decreased weightbearing capability. Prolonged knee extension in the stance phase is another problem that can occur with TF amputations. This extension can result in shortening of the contralateral step and an increase in the vertical displacement of the center of gravity.

If lateral hip thrust is the problem, immediate attention should be given to the wide dimensions of the mediolateral proximal socket that affect the stability of the hip. If the socket fits well, the patient could have weak hip abductors, or the hip adductors might not have been reattached at the time of surgery.

The most prevalent gait abnormality with TF amputations is ipsilateral trunk bending in the stance phase. Similar to the compensation for Trendelenburg gait, this abnormality could indicate weak hip abductors on the ipsilateral side or an inappropriately short prosthesis. Occasionally, a person who has undergone a TF amputation can have an awkward downward movement of the upper body over the prosthesis, especially during fast walking. This is referred to as a drop-off gait in the late stance. The foot of the prosthesis should be checked for excessive dorsiflexion whenever external rotation of the leg occurs, either during heel strike or in the late stance. The foot should be examined for excessively hard materials. As with TT amputations, TF amputations can be associated with some of the same problems in the stance phase; the etiologies of the abnormal biomechanics are similar.

In people who have undergone TF amputations, gait abnormalities in swing phase are limited in number. Stiff-knee gait patterns can be the consequence of excessive knee stability in the joint that makes the creation of a flexion moment at the knee difficult. Circumduction, or the swing of the limb in a wide arc, usually indicates inadequate suspension or excessive length of the prosthesis. Abnormal axis rotation at the knee that results in a whipping motion is usually due to incorrect alignment of the prosthesis at the knee.

Thus, the dynamic alignment process requires not only a keen perception by the alignment personnel, but considerable experience in evaluation the numerous factors. The alignment of every person is different and there are no quantitative guidelines for the subjective optimization.

What is needed, therefore, are techniques for real time dynamic alignment of prosthetics utilizing a smart motion blending algorithms and a blending engine to create a single objectified protocol for the alignment process.

SUMMARY OF THE INVENTION

Various aspects of the present invention represent a new technique and technology for real time alignment of a prosthetic limb to its wearer.

One aspect of the present invention pertains to a method for real time dynamic alignment of a prosthetic limb by a custom system and user interface that allows real time blending of a motion database that contains all the possible alignment errors and enables real time comparison to any specific patient. Data stream coming from the motion database is parsed through a specially written blending algorithm that derives biomechanically correct accelerations and velocities and forward and inverse dynamics resulting in real time display of the error attenuation of a specific patient compared to the alignment errors in the database. Those are passed in real time to a 3D human muscle model making the forces and torques visible to the user as they happen.

Another aspect of the invention involves runtime interaction by a user or operator.

A further aspect of the present invention is a combination of motion capture technologies, simulation technology and custom real time data processing algorithms, using a combination of hardware and software elements combined with the authoring and control software to visualize in real time the errors present in the prosthetic alignment and the needed actions to correct them to achieve optimal objectified dynamic alignment.

Still another aspect of the invention involves a new measurement and visualization tool, bearing applications in various industries. The invention creates the possibility of comparing pre-recorded motion databases of alignment errors against a real time data stream coming from any specific patient and blending the data in real time to achieve optimal dynamic alignment leading to optimal functional performance to a range of given situations.

Yet another aspect of the present invention relates to a platform and tools to analyze human motions in a real-time on-line or web environment, enabling medical experts to understand, treat or predict motions of patients using a web based reference database in combination with the patients' motions. Though in this aspect targeted at above the knee amputees, the invention is highly adaptable for other user groups.

A yet further aspect of the present invention relates to a process that incorporates real time 3D marker data streams coming from a motion capture system through real-time sets of algorithms that derive from the 3D markers cloud the joints' centers of rotation, positions and orientations, then derives accelerations and velocities and compares those with an array of pre-recorded alignment errors that are passed to a 3D human body model on a computer screen, transposing them on top of each other, enabling a therapist to view in real time the offsets present from an optimal alignment and correct the errors, achieving an optimal alignment for any specific patient.

As detailed herein, dynamic alignment of a prosthetic limb is typically a visual estimative process that is subject to the skill and experience of the specialist doing the alignment. It is not an objective quantifiable process and often requires repetitions to achieve an optimal state. One embodiment of the present invention makes it possible to objectify and quantify the process in real-time, in a way that makes clear the offsets and deviations from optimum and enables real time correction to achieve optimal alignment in dynamic conditions.

The process of achieving this functionality relies on fast and accurate real time motion blending engine that compares in real time the data stream coming from any specific patient. A further embodiment of the process is deriving, in real time, the offsets and deviations of the current gait of the specific patient and outputs instructions to the specialists doing the alignment regarding the corrections they need to do to achieve the required optimal alignment.

In another aspect of the invention, the process enables manual blending in real time between the suggested result coming from the blending engine and the incoming data from any specific patient. A final process converts the resulting streams into 3D visualizations of the offsets from an optimal alignment into a 3D accurate human body and prosthetic limb alignment model.

In a further aspect of the invention, the methodology extends to having a system of the invention integrated by wired or wireless means with prosthesis adjustment actuators mounted on or within the prosthesis, controlling the actuators so as to enable computer or operator controlled adjustments to correct alignment errors, while the subject is in motion, and without otherwise interfering with the subject. Onboard actuators may be battery or spring-powered, or motion powered as by walking, or be otherwise sufficiently powered to affect the required adjustments. In still another aspect of the invention, onboard sensors and computer hardware may generate and enable the use of motion data and blending algorithms to dynamically alter the alignment of the prosthetic limb in near real time to fit the changing environment and motion activity of the subject.

Body mounted markers and stationary sensors, or body mounted motion sensors such as inertial motion sensors, whether wireless or wired, and other means of sensing and measuring parameters such as but not limited to body position, alignment, and motion with sufficient resolution to measure limb segment position and alignment in real time, are all within the scope of the invention for capturing the real time alignment and position of the prosthetic limbs and related body motion of prosthesis-equipped subjects.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

Figure 1:
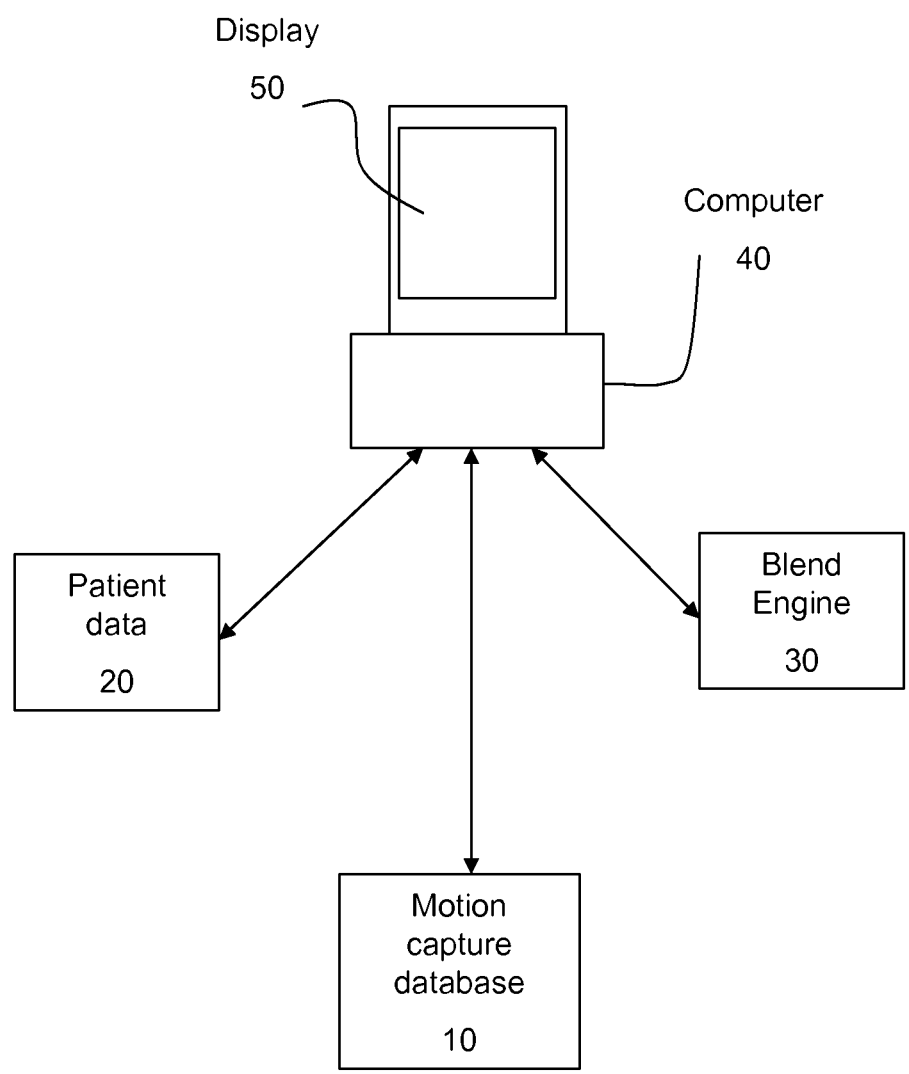
FIG. 1 is block diagram of components for the system configured in accordance with one embodiment of the present invention.

After the static alignment process of a prosthetic, a dynamic alignment is required. The dynamic alignment of a prosthetic limb is typically a visual estimative process that is subject to the skill and experience of the specialist doing the alignment. Such visual observation typically requires viewing the patient commence activity with the prosthetic attached and noting movement and querying the patient about discomfort.

Various embodiments of the present invention provide tools that are useful in numerous applications, including the diagnostic and rehabilitation industries. This system allows or provides for the visualization of possible errors present in the prosthetic alignment for any given movement in real-time.

Motion blending is a term for a variety of techniques. Many motion editing algorithms, including transitioning and multi target interpolation, can be represented as instances of a more general operation called motion blending. Some use data structures called registration curves that expand the class of motions that can be successfully blended without manual input. Registration curves achieve this by automatically determining relationships involving the timing, local coordinate frame, and constraints of the input motions. Registration curves improve upon existing automatic blending methods and demonstrate their use in common blending operations. The technology has existed for several years in a variety of applications.

Kinematics is the process of calculating the position in space of the end of a linked structure, given the angles of all the joints. Inverse Kinematics does the reverse. Given the end point of the structure, it processes angles of the joints necessary to achieve that end point. This process is used in robotics, 3D computer animation and some engineering applications.

Embodiments of the present invention incorporate features of blending and kinematics in order to accomplish the goals of the alignment processing. Some of the benefits include a reduction in the time needed for the alignment of a prosthesis. It permits isolation and the ability to assess separate body parts in a controlled environment. In certain applications, it can be used as an on-line second opinion to confirm the specifications of the alignment personnel. Furthermore, it provides better information and instruction to patients.

According to one embodiment, the present invention enables and contributes for the first time to development of quantified standards in prosthetic diagnosis and treatment of motions that were heretofore only based on a subjective "professional opinion". The system allows the user to forecast motion patterns to improve learning and training curves. And, it provides the patient with information and details concerning the rehabilitation process which may help to establish a more realistic expectation.

The applicant herein incorporates by reference U.S. Pat. Nos. 6,738,065 and 6,774,885 for all purposes. The '065 patent details a system and method for customizable animation wherein a motion capture database houses a library of human motion and users are allowed to select motion sequences and alter these motions in real time. There is blender software used to interpolate and extrapolate from existing library data to create new and original motion sequences that are developed to comply with bio-mechanical laws, physics and human anatomy. In another embodiment, users can bypass the bio-mechanical laws, physics and human anatomy and create mutations of the motion capture data. The algorithm can be implemented to handle perceived optimal motion vector. For example, when a user is choosing the source and the destination of the blended sequence, the source's velocities and accelerations are extrapolated, the reverse happens with the destination's acceleration and velocities. The predictive algorithm offers the user the "most natural" blend interval in time. Finally, the environmental rule sets are implemented, facilitating real-time simulations of the velocity/accelerations variances in response to changing conditions in the environment. Those simulations make use of Lagrange equations in combinations with the velocity base blends discussed herein.

FIG. 1 shows a top-level block diagram of certain elements of one embodiment of the invention. Motion capture library database(s) 10 contains the various motion data such as sequences and actions including those that have been recorded using the optical and magnetic markers as well as a growing volume of motion sequences that have been blended and modified. The database 10 can be a server or other storage mechanism that can reside with the computer 40 or simply be coupled to the computer 40 by wired or wireless connections.

The motion database 10 contains the prosthetic errors/offset possibilities created by producing a motion capture records that extend to the complete set of error types relevant to each motion, in all directions, extending to full range or extreme of each error type. For example, an artificial leg has a finite number of alignment errors which is reflected as being per joint, per direction, or based upon some time dependent errors such as too early lock or to late lock. These motion records reflecting alignment errors or flawed motion are available in a lookup table that is later compared to the data stream from a patient. Such a comparison is done in real time according to one embodiment.

The computer 40 that acts as the administrator of the system. The various other components are interconnected to the computer directly or through a network, wherein a network is defined herein as any means of communicating between devices, including Internet, Intranet, and wireless means.

Patient data 20 is accessible to the computer 40 and is used in conjunction with a template matching algorithm. The patient data can be for example, a video or motion capture data of the patient. Also connected to the computer 40 is the blend engine 30 that encompasses an algorithm that uses forward and inverse kinematics, Lagrange equations and even genetic algorithms to blend the data and produce the realistic motion sequences. The blender 30 functions by implementing the internal basic environment that allows blending between two or more sets of motion capture data, subject to the correct bio-mechanical behavior.

One embodiment of the invention is a method for real time blending by a computer 40 of the array of offsets and errors in a current alignment of a prosthetic limb using 3D animation of a human body and prosthetic limb models. Data streams coming from any specific patient 20 are compared in real time through a pipeline of specially written algorithms to a pre-recorded motion database of motions 10 that contain the possible errors that are manifested in wrong alignment of the elements of the prosthetic limb. The resulting offsets are passed in real time to a 3D human model 50 making the offsets and current alignment errors visible to the eye as they happen.

An aspect of the invention allows runtime interaction by a user or operator. Such an embodiment of the invention can be seen as a combination of motion capture technologies, motion blending technology and custom real time data processing algorithms, using a combination of hardware and software elements combined with the authoring and control software to visualize in real time the offsets and errors present at any given prosthetic alignment for any specific patient.

One embodiment of the invention creates a new measurement and visualization tool, bearing applications in various industries. The invention creates the possibility of looking at blended pre-recorded motion data of dynamic alignment errors of a prosthetic limb for determining, registering and evaluating optimal human functional performance to a range of given situations. Although at least one embodiment of the present invention is intended for medical applications, embodiments of the present invention are adaptable for other market segments.

Figure 2:
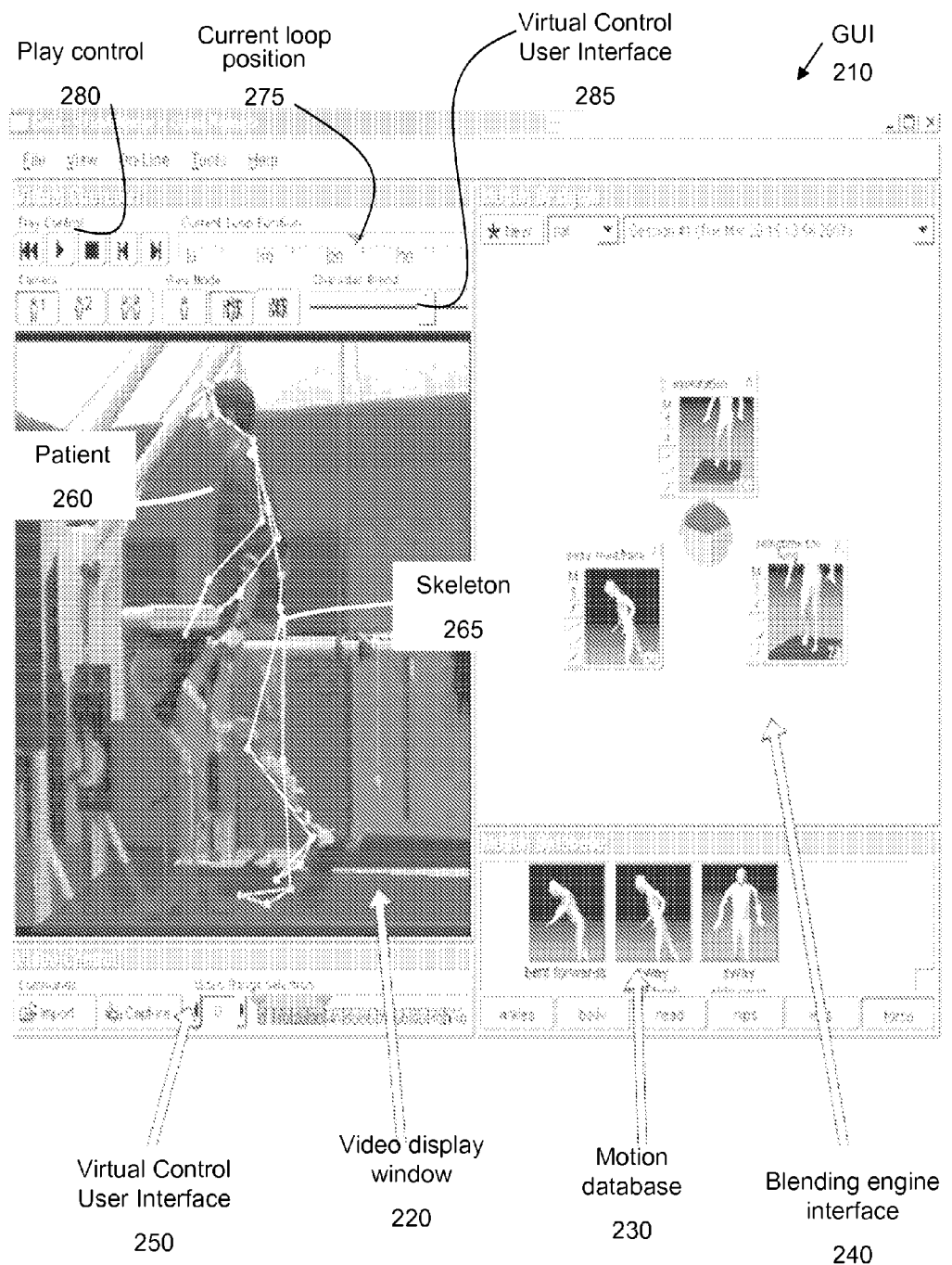
FIG. 2 is an image illustrating a user interface of an application configured in accordance with one embodiment of the present invention.

One embodiment of the present system is illustrated in FIG. 2 which shows a graphical user interface (GUI) 210 with features that can be used to enhance, objectify, quantify, optimize and improve dynamic prosthetic alignment, by providing a real time visualization of the given alignment errors. There is a video overlay window 220 that in this embodiment shows a video of the patient 260 with an overlay of the blended data 265 in a skeletal form. This allows the alignment personnel to see the dynamic alignment errors from the motion database of recorded possible prosthetic alignment errors and offsets 230 of the fitting of the prosthetic limb in order to achieve the desired optimal alignment in an objective, repeatable method. A motion blending engine 240 instantly compares the patient's motion to selected records of known performance and provides immediate offsets and error values to the prosthetist to correct in order to achieve optimal dynamic alignment.

The motion blending according to one embodiment creates a unique and natural motion, by combining a number of pre-defined motions from a motion database 230. For example, each of these depicted individual motions consists of a single stride and represents a specific abnormality. Starting with a 'correct' motion, any combination of abnormalities that is found in a real subject can be reconstructed by blending weighted versions of the relevant motions with the current motion. The weighting and manipulation can be manual, semi-automated or automated.

In more particular detail, in this embodiment, the main application is comprised of several separate modules, namely Virtual Character, Motion Designer, Video Control, and Motion Database.

Virtual Character Module

This module displays your current blend. The currently active body part is highlighted in a specific color. There is also a slider that is used to indicate the current position in the loop of your blend. Controls are provided for play, stop, rewind, step right and step left. The user can press anywhere on the indicator to move to a given position. The appearance of the character (and the background) can be altered via the View Menu commands. The character is rendered using OpenGL. For correct rendering, a video card that supports OpenGL can be used.

Motion Designer Module

The user can change the actual animation, by combining sources from the Motion Database. Sources can be dropped anywhere inside the module to be added. The closer a source is to the center, the more relevance it has and the more influence it asserts on the blend. The amount of influence of each source is indicated by the little pie-chart in the center, as well as by the percentage in the lower right corner of each source. Pressing the new button generates a fresh new blend. The rotation of the treadmill can also be selected.

Motion Database Module

The motion database contains an overview of all the available sources. Sources are sorted by body part (indicated by the buttons on the left). Holding the mouse cursor over any icon allows the user to view the animate movement.

Video Control Module

The video control module allows the user to import an AVI file, or capture one. The video range selection can be used to select a proper loop inside the AVI-file. The length of the loop is fixed, and identical to the length of the blend.

In order to find the optimal reconstruction, two methods are typically employed, namely Manual Reconstruction and Automatic Reconstruction/Semi-Automatic Reconstruction.

Manual Reconstruction. Using this method, a user selects a set of motions by hand and tries to find the correct weighting factors for each motion. The user can use a computer generated animated mesh that represents the current blend, and projects this on top of a video recording of the patient for validation.

Automatic Reconstruction/Semi-Automatic Reconstruction. When actual 3D motion data is available for a specific patient, the optimal combination of motion blends for a specific motion can be found using a search algorithm. This algorithm can utilize the difference in the actual motion sequence and the motion blend as a search criterion.

A video control user interface 250 enables transposing of the incoming video stream of a specific patient into the system which can then be incorporated into the video overlay window.

There are a number of Virtual Character user controls that permit the user to review the data and work on optimization for the alignment. There is a play control 280 to allow the user to move the data forward, backward, or to pause at a given segment. The current loop position 275 is visible to the user. There is a character blend slide bar 285 that can be used to manipulate the virtual character.

According to one embodiment, the patient data will be taken from motion capture data of the patient which may include basic physical description of the patient. Another embodiment uses recorded video of the patient to allow for the overlay. A still further embodiment includes a patient template that can be based upon certain physical properties of the patient and created by the system, empirically derived based on existing patient templates, or by selecting an approximate patient template.

In the state of the art prosthetics alignment for parts of the leg, walking provides the movement that is used for dynamic alignment. The gait of the patient is examined by the alignment professional and a process of alignment and observation continues until the alignment specialist believes the optimal position is obtained. It should be appreciated that while the described embodiment relates to leg prosthetics, the system applies to any artificial limb. For example, the video can be a patient's hand and the blended data would note the various movement points such that a comparison can be made between the patient hand movement and the movement from the motion database.

In the context of one embodiment of the present invention for dynamic alignment, it is also possible to project a video stream of the patient in motion in combination with the alignment error data as illustrated in FIG. 2, taking the data stream from the motion capture system and transposing the video stream on top of it in a matching perspective.

One application for the alignment information is for clinics and doctors that do not have a motion lab and any motion capture equipment. In this embodiment, the system allows a visual matching of the video overlay to see the offsets from an optimal alignment. The video overlay can be, for example, obtained with a webcam or video camera. According to one embodiment the application is web-based.

Once there is a conclusion about the offsets and errors that require correction, the prosthetist makes adjustments to the relevant bolts and spanners on the prosthetic leg to adhere to the output of the system. A verification session can be executed to confirm the alignment.

Figure 3:
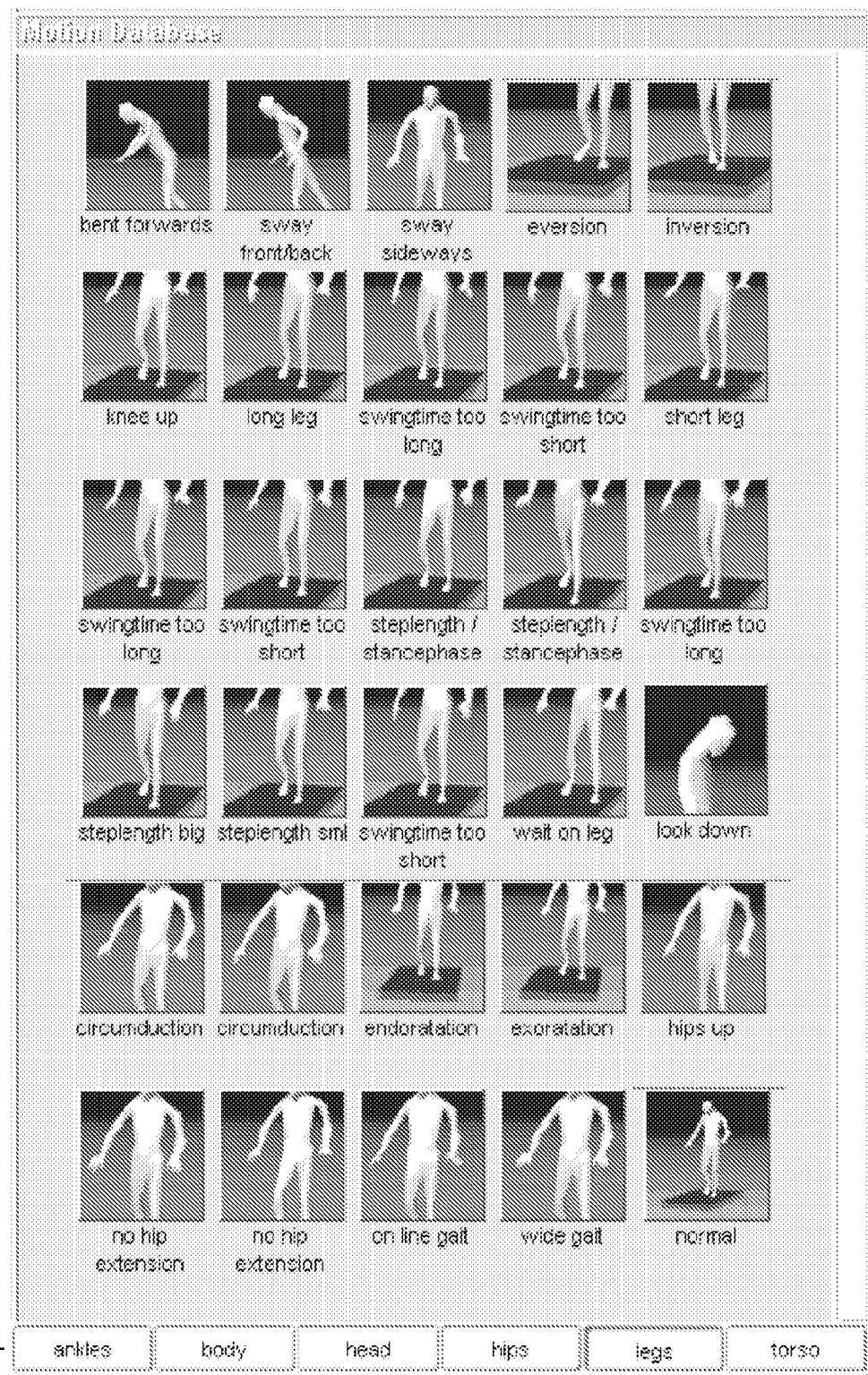
FIG. 3 is a computer generated image showing the motion database of possible alignment errors of a prosthetic limb as manifested on the human body configured in accordance but not limited to one embodiment of the present invention.

Referring to FIG. 3, computer generated images show a portion of the motion database of possible alignment errors of a prosthetic limb as manifested on the human body. There is a menu 300 for each of the main components of the desired analysis, which in this example includes ankles, body, head, hips, legs, knees. The user can dynamically alter or influence the operating parameters by introducing a change from the motion database. There are thumbnail images for an array of abnormalities for any of the main components.

For example, the head can be designated as 'look down' in one of the simulations to instantaneously observe the impact on the persons animated gait. Adjustments to the alignment can then be made if required.

In practice, there are a finite number of errors in tuning and alignment of a prosthetic limb. The majority of the errors are directional with respect to the relevant joints. Some of the errors are related to timing, such as gait cycle dependent, wherein the cycle can be overly long or too short, or there may be a lock mechanism that is too early or too late. There can also be a relation between errors. For example, if a foot is twisted to the outside and the foot/heel joint alignment is optimal, then the error is in the knee joint. This relation is also used internally at the blending engine level. Thus, according to one embodiment the alignment process includes a limited number of directional errors related to a particular joint. The modeling is consistent with normal human behavior thus, for example, it would not be possible to have the head rotate 360 degrees.

According to one embodiment, the operator can run real-time simulations of a variety of different alignment issues and numerous combinations thereof in order to provide a comprehensive alignment. In contrast, the state of the art visual observation process requires the patient to go through a number of different scenarios to obtain a greater sample of movements. However, it is unlikely that a patient would be willing to undergo the time required to attempt all the array of alignment factors.

Figure 4:
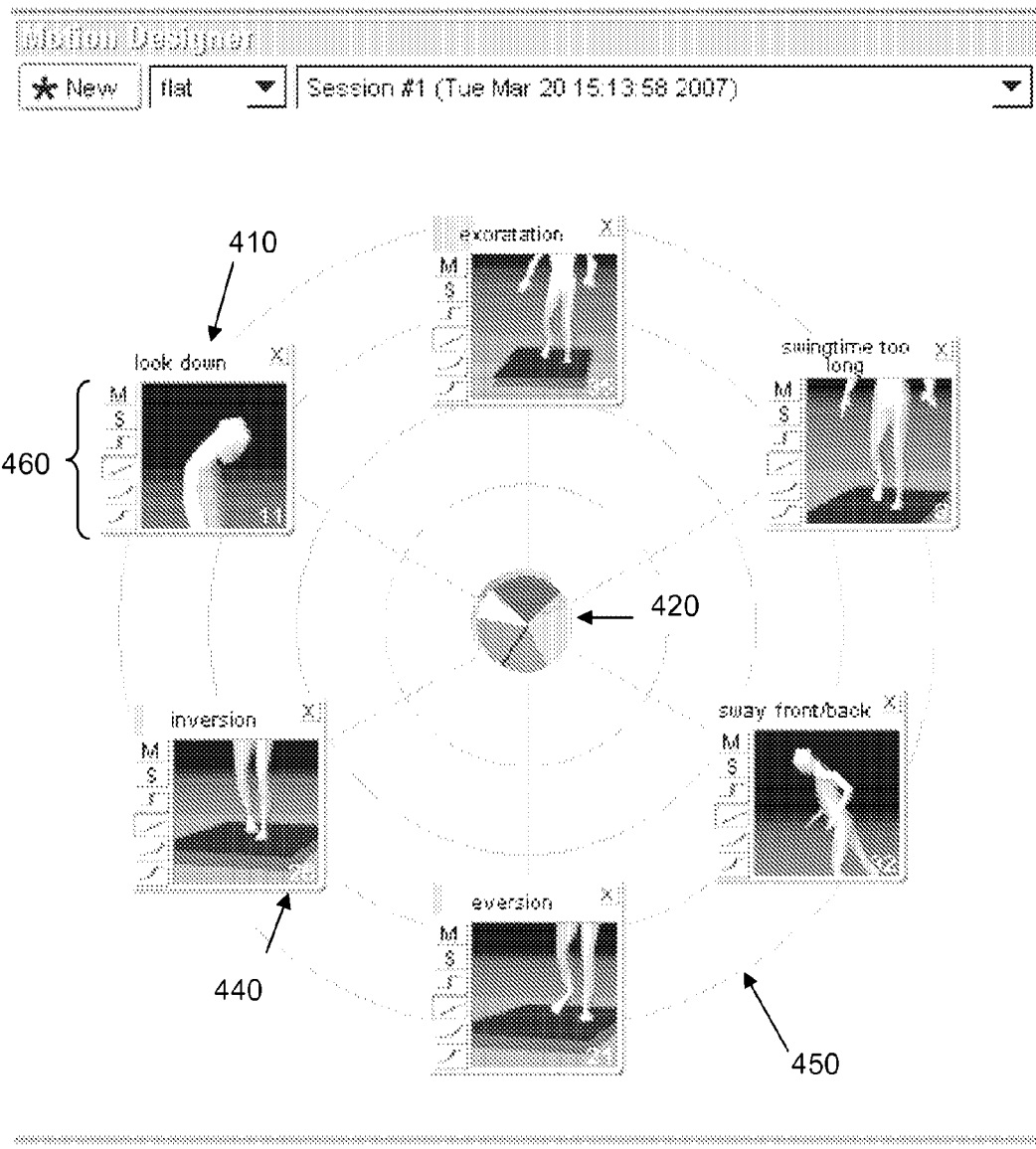
FIG. 4 is a computer generated image illustrating the blending engine that enables the real time blending of possible alignment errors of the prosthetic limb configured in accordance with one embodiment of the present invention.

Referring to FIG. 4, the GUI for the motion designer is described according to one embodiment. The motion designer allows the user to manipulate any of the actual animation, by combining sources from the Motion Database.

In this particular GUI interface 400, a 'pie chart' 450 is presented with a number of movement icon sources 410. Any number of sources 410 can be dropped anywhere inside the module to be added or blended into the animated presentation. The closer a source 410 is to the center 420, the more influence it has on the blend. The amount of influence of each source 410 is indicated by the size of its respective angular slice of the little pie-chart in the center 420, as well as by the percentage box 440 in the lower right corner of each source. A fresh new blend is generated by pressing the 'new' button. The position/rotation of the treadmill can be adjusted by using a selectable box such as the depicted selection 'flat.' Typically the rotation is set before sources are dragged into the motion designer. Each session is recorded and time/date stamped and multiple sessions can be saved, stored and retrieved.

The operation of certain aspects of the present invention are similar to those of the related '065 patent in certain respects but are here related to a clinical application and purpose. The '065 disclosure was related to entertainment modes and applications, and since the present system generally adheres to the actual physical realm, it typically will not allow for a violation of the normal biophysical human model.

The Blending Area interface 460 allows the user to make changes to the data in the blending process. This can be done using sliders and blend types in the Blending Area. The model is broken down by area of the body (i.e. head, shoulders, hands, feet, etc.). Within each area of the body a further breakdown can be accomplished.

The Blending Type controls the amount of "leakage" of motion from the active (currently under editing) body part, to the rest of the body. Since all the sources are made from full body motion capture sequences, the amount and the path of the leakage will create different blends.

By clicking on the leakage icon of the particular item that you want to modify, a pop-up window of leakage blend types appears. Simply click on the desired type to select.

In this embodiment, there are three blend types, Constant, Linear Decay, and Exponential Decay. Constant refers to a full leakage, similar to average mix Linear Decay, wherein depending on the active body part, motion will "leak" down the skeleton hierarchy so that the body parts furthest away from the active body part will be compensated minimally. The leakage icon shows the representation for linear decay under the blending type.

There is Exponential Decay, resulting in less leakage along the body. This is developed to variable decay (velocity based). The leakage icon shows the representation for exponential decay under the blending type.

The slider bar and value display are the key interfaces in the blending process. The user can change the values of each characteristic by clicking or dragging on an associated slider bar. Note that the numerical value to the right adjusts accordingly. A lock checkbox and value display can be used to hold the value of the slider. This is useful when you do not want this value to be modified by any of the other characteristic value changes.

Figure 5:
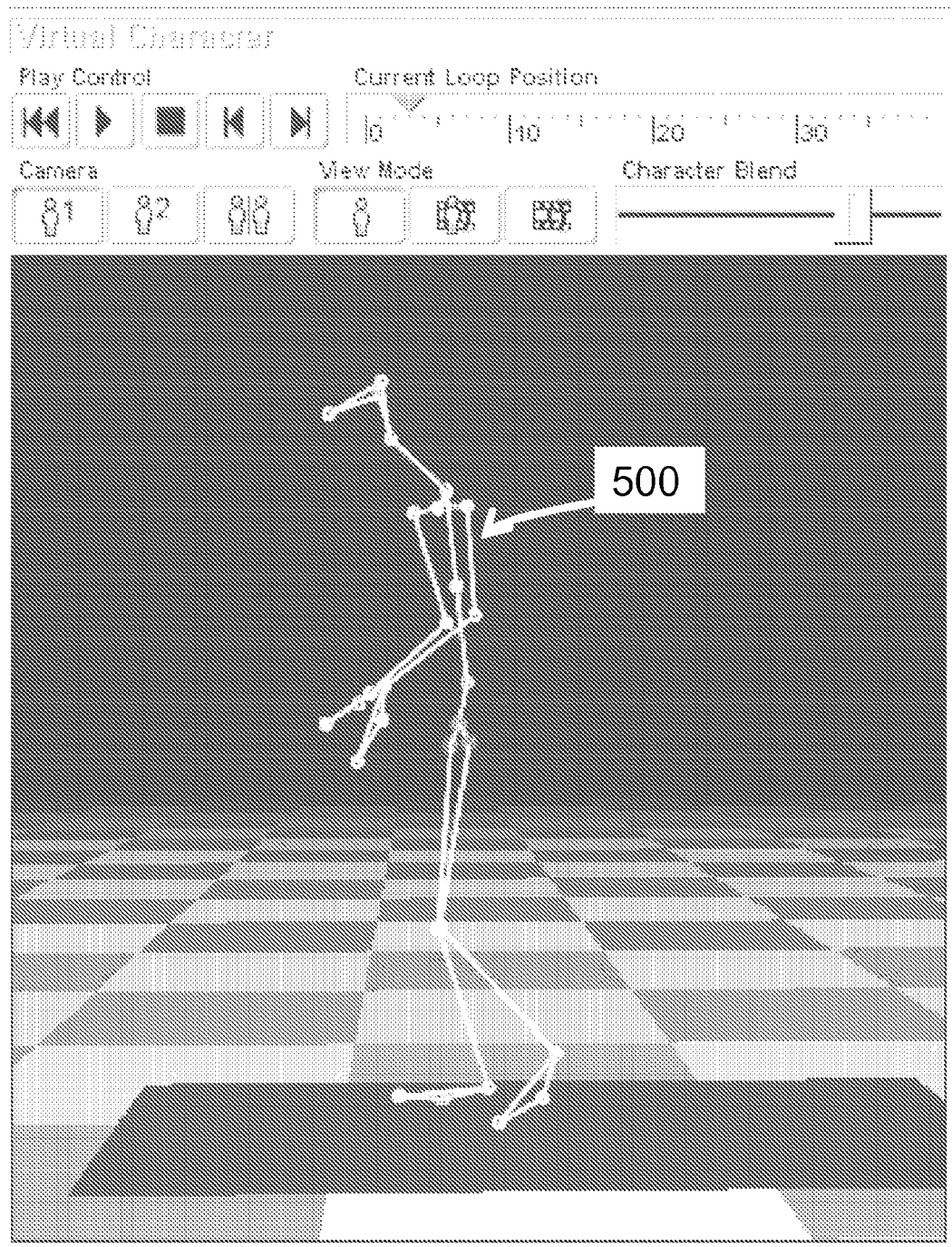
FIG. 5 is a computer generated image illustrating a three dimensional anatomically correct blended model of a virtual character showing the result of the blend on a stick figure with all the body joints configured in accordance with one embodiment of the present invention.

FIG. 5 illustrates a three dimensional anatomically correct blended model 500 of a virtual character showing the results of the blend on a stick figure with all the body joints that have movement. The body joints can be expanded to include more detailed joints and can isolate particular movements about a particular joint.

This figure 500 enables the prosthetist to see errors present in the alignment and to confirm alignment measurements. It allows the user to be able to manually correct for these errors where needed with a visual reference. The system can also display a 3D character for alignment, wherein the stick figure 500 is one representation of the current alignment state. In another embodiment the 3D character can be a 3D rendered mesh and not merely a stick figure.

There are a number of user interface options including play control, blending, camera views and view modes that the user can manipulate to obtain the desired result.

Figure 6A:
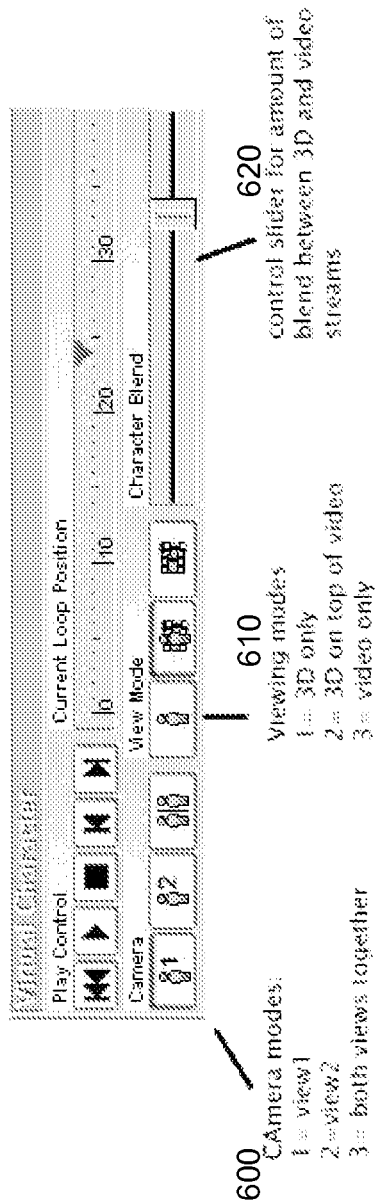
FIG. 6a graphical user interface showing the virtual character tool bar configured in accordance with one embodiment of the present invention.

Referring to FIG. 6a, several of the virtual character viewing and control features are depicted. There are several camera modes 600 wherein the user can employ one view, two views, and even combined views. In the viewing mode 610, the user can view in 3D, 3D overlaid on top of the video, and the video alone. The character blend tool slider 620 allows for the user to adjust the blending between the 3D generation and the video streams.

Figure 6B:
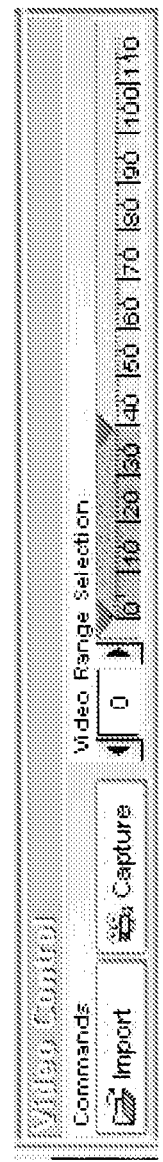
FIG. 6b is a graphical user interface showing the video control tool bar according to one embodiment of the present invention.

FIG. 6b illustrates some of the functionality of the video control features per the GUI. As noted, there is an import feature that allows the user to input various forms of videos. The video can be any of the typical formats and can be input from a computer memory, digital device, and from the web. The system also has the capacity to create the video by using an accessory recording device such as a camera. The image can be captured with recording devices that can be coupled with the system such as a webcam. Such recording devices can be wired or wireless, and in one embodiment is web-based such that the person being recorded is in another location.

Figure 7:
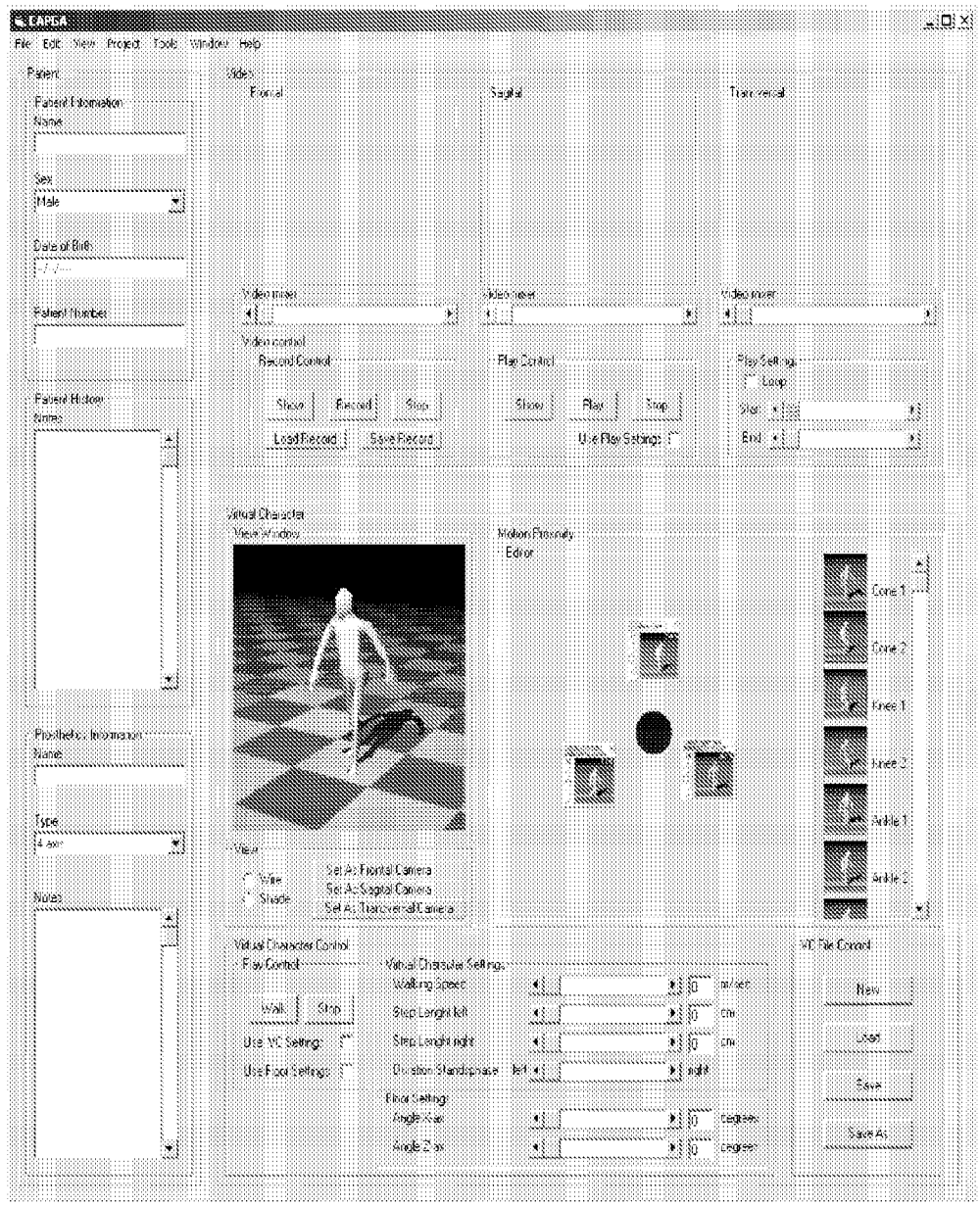
FIG. 7 is a graphical user interface showing the video and virtual viewing interface and options configured in accordance with one embodiment of the present invention.

Referring to FIG. 7, another graphical user interface is depicted. There are input fields for patient information such as name, gender, date of birth and a patient identification number. Some pertinent patient history can be incorporated and can include a description of the artificial limb as well as medical history and allergies. Notes can also be included. Additional fields can include prosthetic information such as the manufacturer, dates of alignments, alignment data, and various prosthetic data.

In this embodiment, there are multiple screens for video display including frontal, sagital and tranversal in order to give multiple views for alignment. Each of the display has a video mixer to alter the parameters and capture the video for later retrieval. The video section interface control in this embodiment includes three video views along with mix controls, record and play options and features.

There is also a virtual character control interface section which can include floor reference, play controls, speed and step length controls, and load/save create controls.

A blend engine interface section in this embodiment includes a slide bar selection tool along with various viewer and motion proximity editors.

Figure 8:
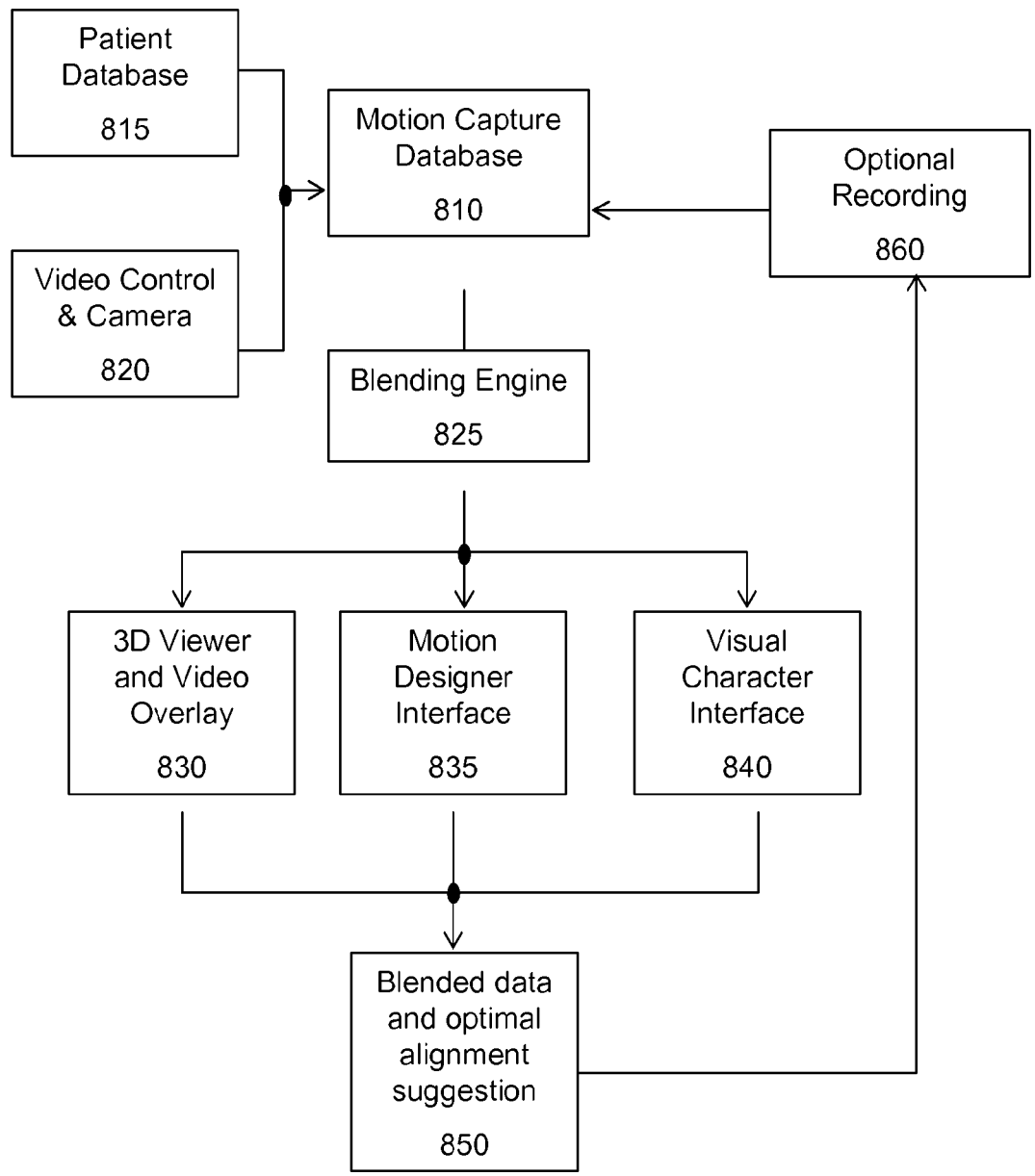
FIG. 8 is a system block diagram showing some of the components according to one embodiment of the present invention.

FIG. 8 shows some of the components of a system according to one embodiment of the invention. Before any blending can be done, one needs an active subject in the patient database 815. This can be done by creating a new subject using the menu, or by loading a subject from the server or from a file. If the user decides to create a new subject, a dialog box appears and allows the user to provide information about the subject. This dialog will reappear when selected.

The user can browse subjects from the server, by selecting Menu subjects. The following dialog will appear: This dialog contains an overview of all available subjects. Any subject can be selected by clicking on it. Pressing the Open button reads the selected subject from the server. Pressing Hide closes this window without opening a subject.

The system includes a capture feature wherein the capturing of video material of subjects is done via a separate application using video control and cameras 820. It can be spawned from the main application by pressing a capture button in the video control section. At any time, the user can press <start capture> to capture a sequence of 3 seconds. After that, the user is asked to revert to the main application, in which the video sequence will be automatically imported.

Pressing the <Add Camera> menu item causes the program to spawn a new capture window, for which another camera can be selected. When working with multiple capture windows, the <Start Capture> button will active all selected cameras simultaneously.

The motion capture database contains all the various possible selection of errors and offsets for the various body parts. The blender 825 is an application that runs through in a separate thread and incorporates data from the motion capture database 810 along with the patient video data. The engine 825 generates the 3D screen with the overlay 830 of the patient data and the captured skeletal data. A virtual character interface 840 allows for manipulation of the virtual character. Each time the user makes a modification in the Motion Designer 835, the parameters are passed on to the Blender engine 825, which in turn generates the 3D animation 830 based on these parameters. The animation is passed back to the main application and is displayed in the Virtual Character section 840.

The blended data, whether manually manipulated, fully automated or semi-automated provides the optimal alignment design 850 to the user. The session can be recorded 860 and communicated to others for confirmation, evaluation or alignment.

Figure 9:
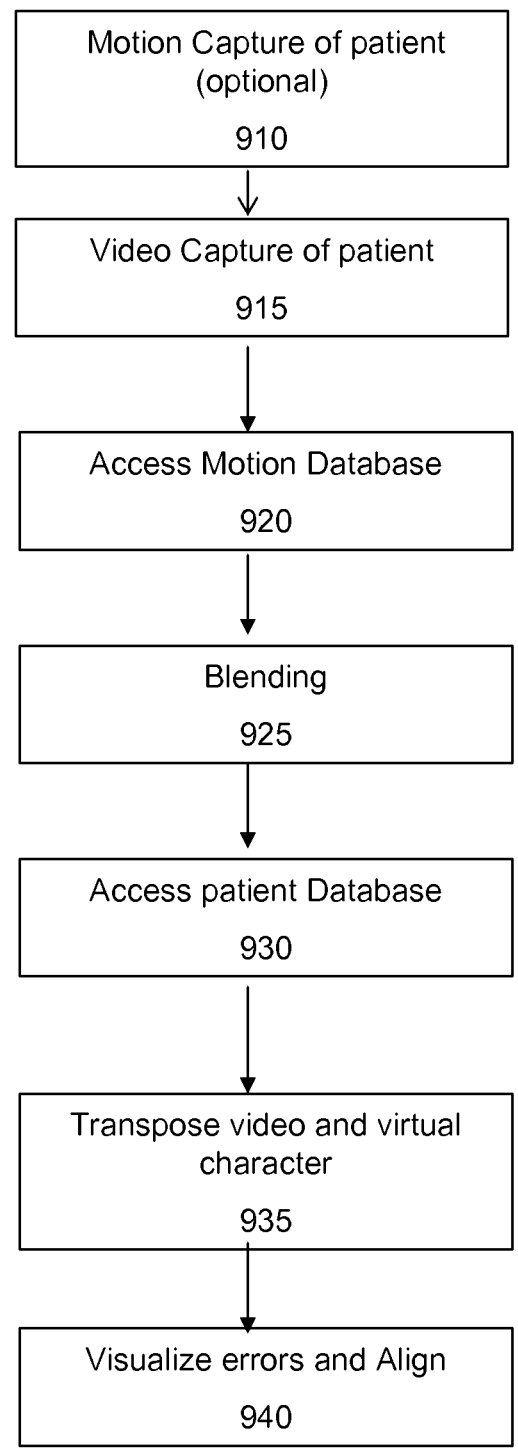
FIG. 9 is a flowchart showing certain steps in the process configured in accordance with one embodiment of the present invention.

Referring to the flowchart of FIG. 9, one embodiment is depicted for the interactive alignment processing. An initial optional step is to equip the patient with optical and/or magnetic markers and capture motion capture 3D data for the patient 910 with the 3D marker data coordinates which can later be used to overlay on the 3D image. The motion capture data can be real time, pre-recorded and even from a web-based feed at another location.

According to one embodiment, a video capture of the patient 1015 can also be used in which a video stream of the patient is used as input for the later transposition. This video data can be used instead of the patient motion capture data or in some cases it can be used along with the patient motion capture data to fine-tune the alignment and confirm the alignment information. Such video can be a live stream such as from a camera or webcam at the alignment site or at another location. The video can also be pre-recorded.

If the patient has motion capture data 910, the 3D motion capture marker data coordinates of a specific patient are sent to the Blending engine for blending 925. The Blending engine receives input from the Motion database 920 in the form of pre-recorded motion data of alignment errors. The motion database contains a library of prosthetic errors/offset possibilities stored in a lookup table.

The Blending engine transmits 3D blended data to the Transposition section for further processing and generation of a virtual character. The transposition section transposes the video with the virtual character and displays the resulting image to the alignment specialist. The video input can come from a video camera or webcam and is displayed as an overlay of the blend (virtual character) on top of the video stream. Between the Blending engine and the transposition section the user can also apply manual blending.

According to one embodiment, the blending engine also sends the blended data to a patient database 930 for registering the patient alignment. The Patient database may contain the specific blended data for comparison to the transposition window for the cases that the same patient is coming for re-alignment. Such prior alignment can be processed by the transposition section and allow for an overlay with the prior alignment data.

The transposition section displays the resulting blend to a visualization screen showing the resulting blend in a form of a virtual character 940, the software also can output the suggested optimal alignment to the specialist. The specialist can then use the data to make the alignment of the prosthetic device.

According to one embodiment, the system processes the optimal alignment and provides this to the prosthetist. Such processed optimal alignment may be satisfactory or at least be sufficiently close so that only minor adjustments are needed.

The methodology of the invention extends to computer controlled adjustments of the prosthesis, based on the calculated corrective values. The alignment may be sensed and the corrections computed externally, as has been described above, and the corrections communicated by wire or wireless means directly from the blending engine and computer in an automated manner in real time, or manually by the operator or prosthetist via a graphic user interface. The control signal goes to an onboard actuator that affects an available adjustment on the prosthesis. The motion detection system detects the change in alignment and re-evaluates the alignment. The process can be a manual step by step or a continuous feedback and control loop as will be understood by those of ordinary skill.

Figure 10:
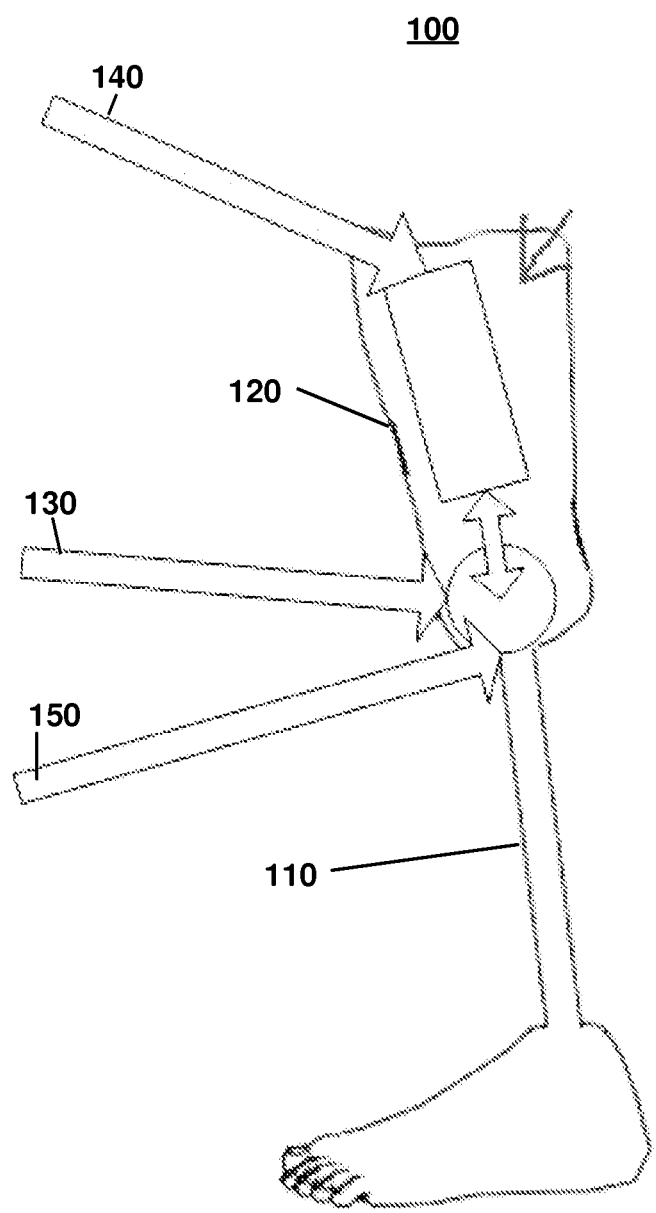
FIG. 10 is a diagrammatic cross section side view of one embodiment of a prosthesis of the invention, illustrating an onboard computer with custom blending algorithms, communicating with a rotational actuator that adjusted

Alternatively, the sensing and blending to produce a corrective alignment may be conducted internally to the prosthesis by an onboard system. Referring to FIG. 10, by way of example, there is illustrated a computer loaded with a blending algorithm of the invention and integrated inside a smart prosthetic limb 100. The smart limb consists of lower leg 110 which is rotationally connected at a knee joint to upper leg 120, allowing rotational alignment and adjustment of swing shift and swing lock of the prosthetic knee. Onboard hardware 140 with custom blending algorithms is mounted within the upper let 120. Actuator 130 provides for rotational correction on Anterior Posterior (AP) and Medio Lateral (ML) planes, by making rotational adjustments of the alignment of lower leg 110 with respect to upper leg 120. Sensor 150 detects the alignment of lower leg 110 to upper leg 120, and any change to the alignment. The output of sensor 150 is communicated to hardware 140 and retained as motion data. In operation, sensor 150 detects error in rotation; blending algorithms in hardware 140 calculate an alignment correction; a command is sent to the rotational actuator 130 to make a suitable adjustment; and sensor 150 reports the correction back to hardware 140.

"Real time," for purposes of the invention, means that the cycle of sensing, blending, and generating the corrective alignment output to the GUI and/or to the prosthesis adjustment actuator is done inside a time span of about 10 milliseconds. This provides essentially continuous, real time sensing, blending, and alignment output during the subject's activity so that what is displayed on the GUI is essentially in sync with the subject's physical motion. Where the actuator is getting real time corrective inputs from the system, the mechanical response of the actuator and resulting prosthesis realignment may add some lag time or hysteresis to the total cycle time required to sense the human response to real time adjustments, but for common human motion activities involving repetitive cycles, such as walking or jogging, the prosthetic adjustments occurring in one cycle of the gait can be assumed to be well settled by the next cycle, when yet a further refinement to alignment may occur.

It will be readily apparent that alternative arrangements of system components are possible, introducing variations on how the methodology is executed. For example, motion sensors may be external of the subject and the prosthesis, or body mounted, or internal to the prosthesis, or any a combination thereof. Sensors may be of various types including but not limited to single or multi-axis position, angular, linear or non-linear displacement, tension, torque, motion, acceleration, pressure, compression, tension, torque, flow and/or any other type of sensor that will contribute to monitoring alignment and performance of the prosthesis-equipped subject, particularly but not exclusively in motion.

Likewise, the computing hardware may be external of the subject and the prosthesis or body mounted or embedded within the prosthesis, or there may be multiple or a combination of computing hardware, such as but not limited to the case where a preliminary dynamic alignment is carried out with external equipment and manual initial adjustments to the prosthesis are made; and thereafter internal sensors and computing hardware operate limited adjustments on the prosthesis in real time to accommodate the variations in the subject's circumstances and activities such as gait, gradient, position, posture, level of exertion, and external load and balance on the subject. Linkages between computing hardware and sensors, graphic user interface, and adjustment actuators may be wired or wireless.

Power, in the case of prosthesis mounted equipment may be but is not limited to converting body heat, spring power, battery power or motion power as by foot movement or reflexing of prosthetic components during motion, or a combination such as by using body and/or prosthetic motion to maintain or recharge a battery or compress a spring.

Semi-automated alignment is also within the scope of the invention. In some cases the patient may have some limitations that the system may not be able to take into account. For example, in multi-trauma patients there may be limitation on the "healthy" limbs or in other parts of the body that make the optimal alignment difficult. In these situations, the system provides a visual reference and allows the operator to edit the results manually for the optimal alignment by taking into account other variables.

A graphical user interface (GUI) display screen for a semi-automated alignment embodiment isolates a particular segment and allows modification of parameters with respect to that segment. For example, three camera views of a prosthesis-equipped subject can be used along with mixing and presentation tools. The GUI includes fields containing patient data and prosthetic information along with a notes field. There is a 3D window along with the various motion capture data of the various body parts. A slider for the floor angle allows the user to incline or decline the walking surface and assess the virtual movement. The display includes alignment, center of mass and ground force which aids in the alignment process. A display option includes a feature to suggest a 3D alignment which automatically makes adjustments to the alignment and the user can then make adjustments if necessary.

One embodiment of the present invention involves a blending engine and a motion database containing a table of possible prosthetic alignment errors which provides therapists with access to extensive exploratory behaviors to achieve proper dynamic alignment and at the same time provide medical experts accurate measurement tools for monitoring the complex process of the alignment in a repeatable objective environment.

The described embodiment offers not only a test and learning environment for patients and doctors, but is also a valuable research environment for motor control. These embodiments open the door to an objective quantifiable clinical protocol of dynamic alignment of prosthetic limbs.

One embodiment of the present invention relates to medical applications. A Gait Analysis Internet Application is one implementation of the system operating in the real-time domain. Such an embodiment pertains to an application in which the full dynamic prosthetic alignment protocols are carried out and evaluated in real time in a variety of reproducible conditions.

One embodiment of the present invention may be utilized by the medical community by making it possible to objectify and standardize the process of dynamic alignment of prosthetic limbs in real-time. It can assist and improve the quality of life of many patients and allow the perception of better physical movement for those not otherwise capable of such motions. In the field of orthopedics and prosthetics, embodiments of the present invention can assist patients in optimizing their present situation, getting a better fit of the prosthetic limb. With orthopedics, prosthetics, and amputees, the system can standardize alignment protocols and improve movements.

Among the features of such an embodiment is the ability to enhance diagnostic and therapeutic activities in a range of medical fields. The enhancements are defined by allowing a medical expert team the opportunity to standardize and objectify the alignment clinical protocols in a controlled real-time environment.

Such a system consists of a combination of a treadmill that is optionally capable of ramping up and down, a computer screen or projection system for the display of the alignment blending database, an optional webcam or a video camera, an optional real time motion capture system and the custom user interface transposing the capture data on top of a video image of the specific patient.

Other and numerous examples of the invention are possible. For example, there is a computer-based system for dynamic alignment of prosthetic limbs for a subject configured therewith, consisting of: means for obtaining motion data of a prosthesis-equipped subject; a motion database with multiple motion records having known prosthetic alignment errors; a motion blending engine configured for blending the motion data with selected motions with known prosthetic alignment errors from the motion database into blended data and a computer configured for receiving the blended data from the blending engine, where the computer is configured to calculate a prosthesis alignment error correction for the subject from the blended data.

The system may have a graphic user interface in communication with the computer for visually displaying the calculated prosthesis alignment error correction. There may be a prosthesis alignment adjustment mechanism in communication with the computer for receiving and responding to the calculated prosthesis alignment error correction. The means for obtaining motion data may be a motion detection system for monitoring motion of the subject, where the motion detection system is linked for communicating the motion data in real time to the motion database and hence to the blending engine.

The motion detection system may have at least one motion sensor external to the prosthesis. It may have at least one motion sensor integrated with the prosthesis. It may be or include an instrumented treadmill upon which the subject moves.

The motion database, blending engine, computer, and prosthesis alignment adjustment mechanism may all be integrated with the prosthesis. The system may consist or include a computer program with a Virtual Character module, a Motion Designer module, a Video Control module, and a Motion Database module.

As another example of the invention, there is a method for computing a prosthetic alignment error correction in real time for a prosthesis-equipped subject, consisting of: collecting motion data from a prosthesis-equipped subject in motion; comparing in real time the motion data with records of motions with known prosthetic alignment errors to determine matching records; blending the motion data with the matching records into blended data and computing in real time from the blended data a computed prosthesis alignment error correction. The method may include outputting the computed prosthesis alignment error correction to a graphic user interface, and/or to an alignment adjustment mechanism in the prosthesis.

The method may include using a camera-based motion detection system to monitor the subject in motion. It may include using sensors integrated with the prosthesis, with the sensors outputting the motion data of the subject in motion to a motion database and hence to a blending engine. The method may include using a motion detection system for the collecting, linked to a motion database for the comparing, linked to a motion blending engine for the blending, linked to a computer for the computing, wherein the method is conducted in real time.

As yet another example, there is a computer system for dynamic alignment of prosthetic limbs for a prosthesis-equipped subject, consisting of: a motion detection system for monitoring a prosthesis-equipped subject in motion, the output of which is real time motion data a motion database configured for comparing subject's motion data to a database of motions with known prosthetic alignment errors and selecting motions based on matching prosthetic alignment errors; a motion blending engine configured for blending said motion data with the selected motions in real time into blended data and a computer receiving the blended data from the blending engine, the computer being configured to calculate in real time a dynamic prosthesis alignment error for the prosthesis-equipped subject from the blended data and to visually display in real time the dynamic prosthesis alignment error on a graphic user interface.

And still another example of the invention is a method for determining alignment adjustments for the prosthesis of a prosthesis-equipped subject, that includes: collecting motion data from a prosthesis-equipped subject in motion; comparing the subject's motion data to a database of records of motion with known prosthetic alignment errors to identify related records; blending the subject's motion data with the related records to create blended data computing from the blended data the prosthetic alignment errors of the subject in motion; and utilizing the computed prosthetic alignment errors of the subject in motion for determining corrective adjustments to the prosthesis. The method may be conducted with a computer-based system in real time, the corrective adjustments being outputted to a GUI.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description.

What is claimed is:

1. A computer-based system for dynamic alignment of a prosthetic limb for a human subject configured therewith, the computer-based system comprising:
    a measurement system for obtaining a patient human motion capture record of a prosthesis-equipped human subject in motion;
    a motion database comprising a plurality of reference human motion capture records that correspond with a plurality of known prosthetic alignment errors;
    a motion blending engine configured for blending said reference human motion capture records, said blending including at least one of weighting and combining said reference capture records, to produce a predicted human motion capture record; and
    a computer configured for comparing the predicted human motion capture record with the patient human motion capture record, said computer being configured to calculate from the comparison a prosthesis alignment error correction for the prosthesis-equipped subject.

2. The system of claim 1, further comprising a graphic user interface in communication with the computer for visually displaying the calculated prosthesis alignment error correction.

3. The system of claim 1, further comprising a prosthesis alignment adjustment mechanism in communication with the computer for receiving and responding to the calculated prosthesis alignment error correction.

4. The system of claim 1, said measurement system for obtaining human motion data comprising a human motion detection system for monitoring motion of said subject, said human motion detection system being linked for communicating the human motion data in real time to said human motion database and hence to said blending engine.

5. The system of claim 4, said human motion detection system comprising at least one motion sensor external to the prosthesis.

6. The system of claim 4, said human motion detection system comprising at least one motion sensor integrated with the prosthesis.

7. The system according to claim 4, said human motion detection system comprising an instrumented treadmill.

8. The system according to claim 3, said human motion database, blending engine, computer, and prosthesis alignment adjustment mechanism being integrated with the prosthesis.

9. The system according to claim 1, the computer being linked with the motion database whereby the patient human motion capture record and the calculated prosthesis alignment error correction for the subject may be recorded therein as a said human motion with known prosthetic alignment error.

10. The system according to claim 1, further comprising a computer program comprising a Virtual Character module, a Motion Designer module, a Video Control module, and a Motion Database module.

11. A method for computing a prosthetic alignment error correction in real time for a prosthesis-equipped human subject, said method comprising:
    collecting a patient human motion capture record from the prosthesis-equipped human subject in motion;
    comparing in real time the patient human motion capture record with a plurality of reference human motion capture records that correspond with known prosthetic alignment errors to determine matching records;
    blending said reference human motion capture records into blended data that approximates the patent human motion capture record, said blending including at least one of weighting and combining a plurality of said reference human motion capture records; and
    computing in real time from said blended data a computed prosthesis alignment error correction.

12. The method according to claim 11, further comprising: outputting said computed prosthesis alignment error correction to a graphic user interface.

13. The method according to claim 11, further comprising:
outputting said computed prosthesis alignment error correction to an alignment adjustment mechanism in said prosthesis.

14. The method according to claim 11, said collecting motion data comprising using a camera-based human motion detection system to monitor the subject in motion.

15. The method according to claim 11, said collecting human motion data comprising using sensors integrated with the prosthesis, said sensors outputting the human motion data of the subject in motion to a human motion database and hence to a blending engine.

16. The method according to claim 11, said method comprising using a human motion detection system for the collecting, linked to a human motion database for the comparing, linked to a human motion blending engine for the blending, linked to a computer for the computing, wherein the method is conducted in real time.

17. The method according to claim 12, said collecting human motion data comprising using an instrumented treadmill upon which the subject moves, linked to a human motion database.

18. A computer system for dynamic alignment of prosthetic limbs for a prosthesis-equipped human subject, the computer system comprising:
   a human motion detection system for monitoring the prosthesis-equipped human subject while in motion, the output of which is real time patient human motion data;
   a human motion database configured for comparing the real time patient human motion data with a database of reference human motion capture records corresponding with known prosthetic alignment errors, and selecting reference human motion capture records from the database based on matching prosthetic alignment errors;
   a human motion blending engine configured for blending the selected reference human motion capture records in real time into blended data that approximates the real time patient human motion data, said blending including at least one of weighting and combining a plurality of said reference human motion capture records; and
   a computer receiving the blended data from the blending engine, said computer being configured to calculate in real time a dynamic prosthesis alignment error for the prosthesis-equipped subject from the blended data and to visually display in real time the dynamic prosthesis alignment error on a graphic user interface.

19. A method for determining alignment adjustments for the prosthesis of a prosthesis-equipped human subject, said method comprising:
   collecting patient human motion data from the prosthesis-equipped human subject in motion;
   comparing the patient human motion data to a database of reference human motion capture records corresponding with known prosthetic alignment errors to identify related capture records;
   blending the related capture records to create blended data that approximates the patient human motion data, said blending including at least one of weighting and combining a plurality of said related capture records;
   computing from the blended data the prosthetic alignment error of the subject in motion; and
   utilizing the computed prosthetic alignment error of the subject in motion for determining a corrective adjustment to the prosthesis.

20. The method of claim 19, said method being conducted with a computer-based system in real time, the corrective adjustments being outputted to a GUI.

* * * * *